(12) United States Patent
Yoshino

(10) Patent No.: US 12,402,781 B2
(45) Date of Patent: Sep. 2, 2025

(54) FOCUS CONTROL DEVICE, OPERATION METHOD OF FOCUS CONTROL DEVICE, AND STORAGE MEDIUM

(71) Applicant: OLYMPUS CORPORATION, Tokyo (JP)

(72) Inventor: Koichiro Yoshino, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 494 days.

(21) Appl. No.: 17/865,653

(22) Filed: Jul. 15, 2022

(65) Prior Publication Data
US 2022/0346636 A1 Nov. 3, 2022

Related U.S. Application Data (63) Continuation of application No. PCT/JP2020/001892, filed on Jan. 21, 2020.

(51) Int. Cl.
| | |
|---|---|
| *A61B 1/00* | (2006.01) |
| *G02B 7/09* | (2021.01) |
| *G02B 23/24* | (2006.01) |
| *G06T 7/00* | (2017.01) |

(52) U.S. Cl.
CPC ...... *A61B 1/00188* (2013.01); *A61B 1/00096* (2013.01); *G02B 23/243* (2013.01); *G06T 7/0012* (2013.01); *G06T 2207/10068* (2013.01)

(58) Field of Classification Search
None
See application file for complete search history.

(56) References Cited

U.S. PATENT DOCUMENTS

| | | | |
|---|---|---|---|
| 2005/0007486 A1* | 1/2005 | Fujii | H04N 23/635 |
| | | | 348/E5.045 |
| 2011/0228064 A1 | 9/2011 | Sasaki | |

(Continued)

FOREIGN PATENT DOCUMENTS

| | | |
|---|---|---|
| JP | 2002-253488 A | 9/2002 |
| JP | 2004-045725 A | 2/2004 |

(Continued)

OTHER PUBLICATIONS

International Search Report dated Mar. 24, 2020 received in PCT/JP2020/001892.

*Primary Examiner* — Beniyam Menberu
(74) *Attorney, Agent, or Firm* — Scully, Scott, Murphy & Presser, P.C.

(57) ABSTRACT

A focus control device includes a processor. The processor analyzes detection results of a target object in time sequence to determine whether the target object is in a lost state in which the target object is not temporarily captured into an image, sets a focus drive mode to an autofocus mode when the target object is detected, sets a first positional mode in which the focus lens is arranged at a position that is within a set range of an in-focus object plane position and is on the far point side of a central position when the target object is not detected and is not in the lost state, and sets the focus drive mode such that a lens position is nearer to a near point than in the first positional mode or sets the focus drive mode to the autofocus mode in a when the lost state is determined.

11 Claims, 7 Drawing Sheets

(56) References Cited

U.S. PATENT DOCUMENTS

| | | | |
|---|---|---|---|
| 2012/0314958 A1* | 12/2012 | Ohwa | G06T 5/50 |
| | | | 382/197 |
| 2015/0304551 A1* | 10/2015 | Funamoto | H04N 23/61 |
| | | | 348/349 |
| 2016/0014328 A1 | 1/2016 | Rokutanda | |
| 2018/0092518 A1* | 4/2018 | Yaguchi | A61B 1/041 |
| 2018/0348470 A1* | 12/2018 | Suzuki | H04N 23/675 |

FOREIGN PATENT DOCUMENTS

| | | |
|---|---|---|
| JP | 2004-205981 A | 7/2004 |
| JP | 2011-193983 A | 10/2011 |
| JP | 2013-183836 A | 9/2013 |
| JP | 2014-188223 A | 10/2014 |
| WO | 2013/061939 A1 | 5/2013 |
| WO | 2019/106712 A1 | 6/2019 |

\* cited by examiner

FOCUS CONTROL DEVICE, OPERATION METHOD OF FOCUS CONTROL DEVICE, AND STORAGE MEDIUM

CROSS REFERENCE TO RELATED APPLICATION

This application is a continuation of International Patent Application No. PCT/JP2020/001892, having an international filing date of Jan. 21, 2020, which designated the United States, the entirety of which is incorporated herein by reference.

BACKGROUND

Endoscopic systems are required to have as a large depth of field as possible so as not to interfere with users' diagnosis and treatment. In recent years, however, the use of imaging elements with high pixel count in endoscopic systems results in a decrease in the depth of field, and users may need to make focus adjustments accordingly.

In order to reduce a burden of focus adjustment on users, endoscopic systems with an autofocus (AF) function have been proposed. For example, JP 2004-205981A proposes an endoscopic system that determines the approach and separation of an object using an optical flow calculated from an image, and controls the start and end of an AF operation based on the determination. The technique described in JP 2004-205981A eliminates users having to perform switch operations for the start and end of the AF operation.

The target object of an endoscopic system is an alimentary canal that generally has a significantly large distance distribution in the depth direction and shape variation over time. According to the technique described in JP 2004-205981A, an AF operation will be started even when the object approaches or separates within the depth of field. That is, an AF operation may be performed in situations without the need for an AF operation.

SUMMARY

In accordance with one of some aspect, there is provided a focus control device comprising a processor, the processor performs: acquiring an image; detecting target object information from the image; and executing a focus control and setting a focus drive mode, and the processor performs: analyzing detection results of a target object in time sequence to determine whether the target object is in a lost state in which the target object is not temporarily captured into the image; setting the focus drive mode to an autofocus mode in which a focus lens is controlled so as to focus on the target object in a case where the target object is detected; setting a first positional mode in which the focus lens is arranged at a position that is within a set range of an in-focus object plane position and is on the far point side of a central position in a case where the target object is not detected and is not in the lost state; and setting the focus drive mode such that a lens position is nearer to a near point than in the first positional mode or setting the focus drive mode to the autofocus mode in a case where the lost state is determined.

In accordance with one of some aspect, there is provided an operation method of a focus control device comprising a processor, the processor performs: acquiring an image; detecting target object information from the image; and analyzing detection results of the target object in time sequence to determine whether the target object is in a lost state in which the target object is not temporarily captured into the image, wherein the processor performs: setting a focus drive mode to an autofocus mode in which a focus lens is controlled so as to focus on the target object in a case where the target object is detected; setting a first positional mode in which the focus lens is arranged at a position that is within a set range of an in-focus object plane position and is on the far point side of a central position in a case where the target object is not detected and is not in the lost state; and setting the focus drive mode such that a lens position is nearer to a near point than in the first positional mode or setting the focus drive mode to the autofocus mode in a case where the lost state is determined.

In accordance with one of some aspect, there is provided a storage medium that stores an operation program of a focus control device comprising an image acquisition section, a target object information acquisition section, and a focus drive mode setting section, the operation program causing the focus control device to operate such that: the image acquisition section acquires an image; the target object information acquisition section detects target object information from the image; the target object information acquisition section analyzes detection results of a target object in time sequence to determine whether the target object is in a lost state in which the target object is not temporarily captured into the image; and the focus drive mode setting section performs: setting a focus drive mode to an autofocus mode in which a focus lens is controlled so as to focus on the target object in a case where the target object is detected; setting a first positional mode in which the focus lens is arranged at a position that is within a set range of an in-focus object plane position and is on the far point side of a central position in a case where the target object is not detected and is not in the lost state; and setting the focus drive mode such that a lens position is nearer to a near point than in the first positional mode or setting the focus drive mode to the autofocus mode in a case where the lost state is determined.

DESCRIPTION OF EXEMPLARY EMBODIMENTS

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Exemplary embodiments are described below. Note that the following exemplary embodiments do not in any way limit the scope of the content defined by the claims laid out herein. Note also that all of the elements described in the present embodiment should not necessarily be taken as essential elements.

1. First Embodiment

1.1 System Configuration Example

Figure 1:
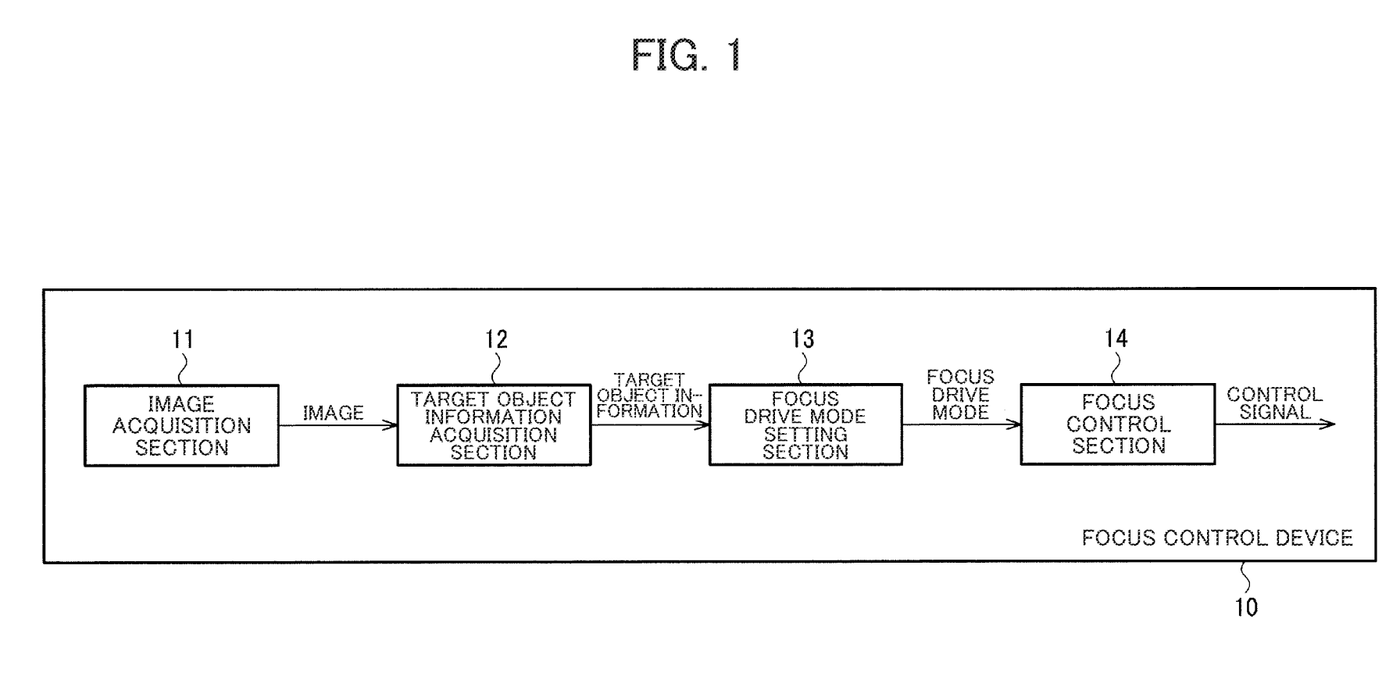
FIG. 1 illustrates a configuration example of a focus control device.

FIG. 1 is a diagram illustrating a configuration of a focus control device 10 in the present embodiment. The focus control device 10 includes an image acquisition section 11, a target object information acquisition section 12, a focus drive mode setting section 13, and a focus control section 14. However, the focus control device 10 is not limited to the configuration illustrated in FIG. 1, and can be modified in various manners such as omitting some of these components or adding other components.

The image acquisition section 11 acquires an image to be processed. The image here is an image captured by an optical system, which is a target of focus control by the focus control device 10. The optical system in the present embodiment is provided in an insertion section 100 of an endoscopic system 20 described later with reference to FIG. 2. The captured image is specifically an in-vivo image obtained by imaging the inside of a living body.

The target object information acquisition section 12 acquires target object information on a target object from the image. The target object information includes information indicating whether the target object is detected and information indicating the position of the target object in the image. As described later in relation to second and third embodiments, the target object information may include information on a lost state and information on whether the target object is within a depth of field.

The focus drive mode setting section 13 sets a focus drive mode based on the target object information. The focus control section 14 performs focus control based on the focus drive mode. Specifically, the focus control section 14 outputs a control signal for controlling a focus lens.

When the target object information acquisition section 12 detects the target object, the focus drive mode setting section 13 sets the focus drive mode to an AF mode. The AF mode is a mode in which the focus lens is controlled to focus on the target object. When the target object information acquisition section 12 does not detect the target object, the focus drive mode setting section 13 sets the focus drive mode to a first positional mode. The first positional mode is a mode in which the focus lens is held at a predetermined lens position. The predetermined lens position here is a preset fixed position. Thus, if the lens position at the time of shift to the first positional mode is different from the predetermined lens position, the focus control section 14 controls the focus lens to move from the current position to the predetermined lens position.

According to the technique in the present embodiment, the focus drive mode is automatically set depending on whether the target object is detected. Since the user does not have to set the focus drive mode manually, it is possible to reduce a burden on the user in focus control. In addition, since the AF mode is used when the target object is detected and the first positional mode is used when the target object is not detected, it is possible to set the appropriate focus drive mode in accordance with the user's usage situation.

Figure 2:
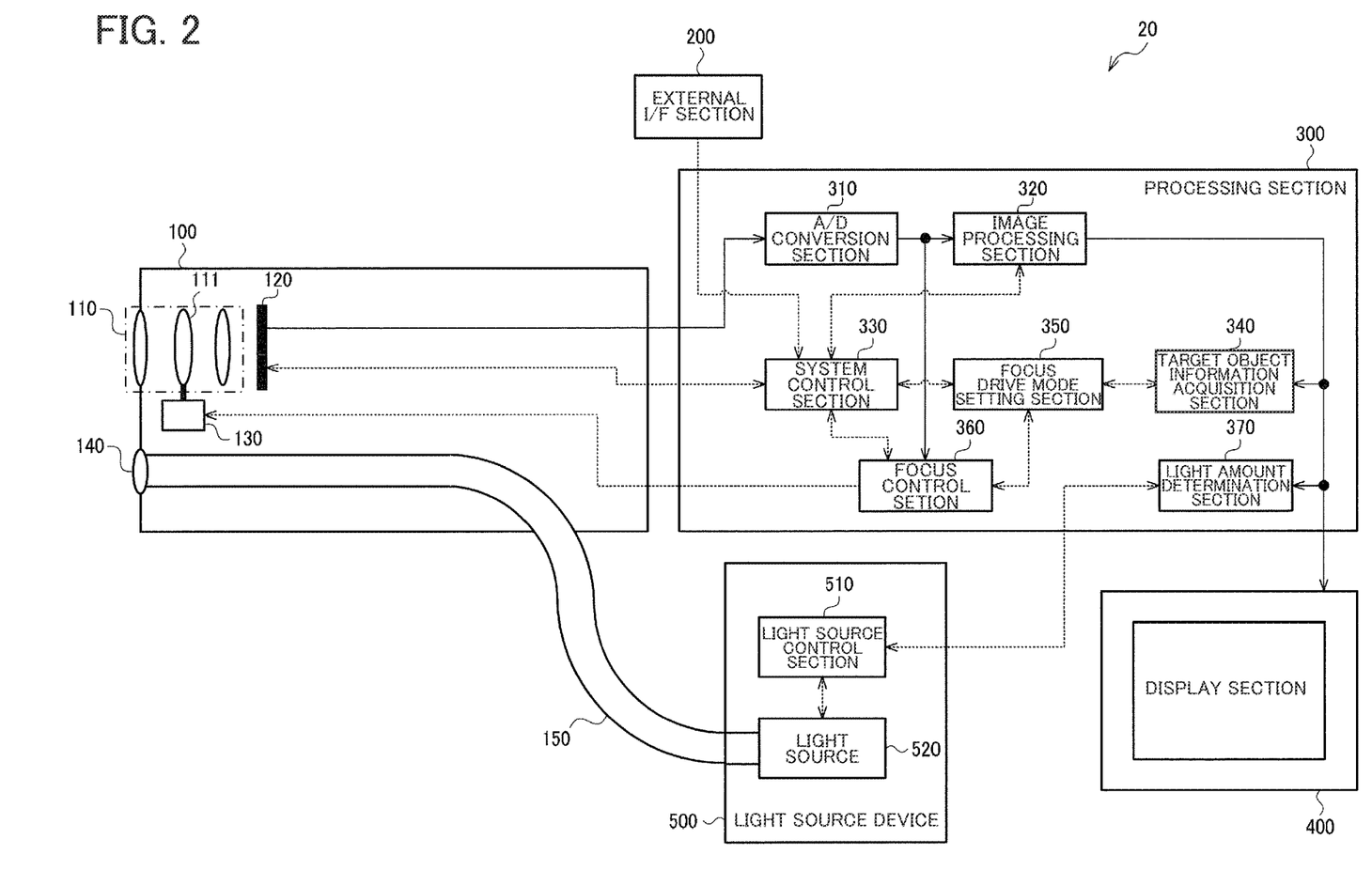
FIG. 2 illustrates a configuration example of an endoscopic system.

Hereinafter, the present embodiment will be specifically described taking the endoscopic system 20 as an example. FIG. 2 illustrates a detailed configuration example of the endoscopic system 20. The endoscopic system 20 includes the insertion section 100, an external I/F section 200, a processing section 300, a display section 400, and a light source device 500. The focus control device 10 illustrated in FIG. 1 corresponds to, for example, the processing section 300 illustrated in FIG. 2. The image acquisition section 11 corresponds to an A/D conversion section 310. The target object information acquisition section 12 corresponds to a target object information acquisition section 340. The focus drive mode setting section 13 corresponds to a focus drive mode setting section 350. The focus control section 14 corresponds to a focus control section 360.

The insertion section 100 is a section to be inserted into a human body. The insertion section 100 includes an objective optical system 110, an imaging element 120, an actuator 130, an illumination lens 140, and a light guide 150.

The light guide 150 guides illumination light from a light source 520 to an end of the insertion section 100. The illumination lens 140 irradiates the object with the illumination light guided by the light guide 150. The objective optical system 110 forms reflection light from the object into an object image. The objective optical system 110 includes a focus lens 111, and can change an in-focus object plane position in accordance with the position of the focus lens 111. The actuator 130 drives the focus lens 111 under instructions from the focus control section 360.

The in-focus object plane position here refers to the position of an object where a system including a lens system, an image surface, and the object is in an in-focus state. For example, assuming that the image surface is the surface of an imaging element, the in-focus object plane position refers to the position of the ideally in-focus object in an image that is captured by the imaging element via the lens system. More specifically, the image captured by the imaging element refers to an in-focus image of the object located within the depth of field including the in-focus object plane position. The in-focus object plane position is the position of an in-focus object, and thus may be also called in-focus position.

The imaging element 120 may be a monochrome sensor or an element including color filters. The color filters may be widely known Bayer-arrangement filters, complementary filters, or other filters. The complementary filters are filters including cyan, magenta, and yellow filters.

The external I/F section 200 is an interface for user input into the endoscopic system 20. The external I/F section 200 includes, for example, a setting button for AF area, an adjustment button for image processing parameters, and the like. The AF area is an area that is used for calculation of an AF evaluation value in the AF mode.

The processing section 300 performs image processing and controls the entire system. The processing section 300 includes the A/D conversion section 310, an image processing section 320, a system control section 330, the target object information acquisition section 340, the focus drive mode setting section 350, the focus control section 360, and a light amount determination section 370.

The processing section 300 (the focus control device 10) in the present embodiment includes hardware described below. The hardware may include at least one of a circuit that processes digital signals and a circuit that processes analog signals. For example, the hardware can be formed of one or more circuit devices and one or more circuit elements mounted on a circuit board. The one or more circuit devices are, for example, ICs, field-programmable gate arrays (FPGAs), or the like. One or more circuit elements are, for example, resistors, capacitors, or the like.

The processing section 300 (the focus control device 10) may be implemented by a processor described below. The endoscopic system 20 in the present embodiment includes a memory that stores information and a processor that operates based on the information stored in the memory. The information includes, for example, programs and various kinds of data, and the like. The processor includes hardware. The processor can be any of various processors such as a central processing unit (CPU), a graphics processing unit (GPU), and a digital signal processor (DSP). The memory may be a semiconductor memory such as static random access memory (SRAM) or dynamic random access memory (DRAM), a register, a magnetic storage device such as a hard disk drive (HDD), or an optical storage device such as an optical disc device. For example, the memory stores computer-readable instructions, and the functions of components of the endoscopic system 20 are implemented as processes by the processor executing the instructions. The components of the endoscopic system 20 are specifically the components of the processing section 300, including the A/D conversion section 310, the image processing section 320, the system control section 330, the target object information acquisition section 340, the focus drive mode setting section 350, the focus control section 360, and the light amount determination section 370. The instructions here may be a set of instructions constituting programs, or may be instructions for instructing the hardware circuit in the processor to perform operations. The processing section 300 may be entirely or partially implemented by cloud computing so that an image can be acquired via a network and the focus drive mode can be set based on the image in the cloud computing system.

The components of the processing section 300 in the present embodiment may be implemented as program modules operating on the processor. For example, the target object information acquisition section 340 is implemented as an image processing module. The focus drive mode setting section 350 is implemented as a focus drive mode setting module. The focus control section 360 is implemented as a control module of the focus lens 111. As described later, the target object information acquisition section 340 may be a module that performs a process using a trained model. The trained model is a program module that is part of artificial intelligence software.

Programs for implementing the processes performed by the components of the processing section 300 in the present embodiment can be stored in, for example, an information storage device that is a computer-readable medium. The information storage device can be implemented by, for example, an optical disc, memory card, HDD, or semiconductor memory. The semiconductor memory is a ROM, for example. The processing section 300 performs various processes in the present embodiment, based on the programs stored in the information storage device. That is, the information storage device stores programs for causing a computer to function as the components of the processing section 300. The computer is an apparatus that includes an input device, a processing section, a storage section, and an output section. The programs are programs for causing the computer to execute the processes of components of the processing section 300. Specifically, the programs according to the present embodiment are programs for causing the computer to execute steps described later with reference to FIGS. 4 and 5 and the like.

The A/D conversion section 310 converts analog signals output in sequence from the imaging element 120 into digital images, and outputs in sequence to the image processing section 320 and the focus control section 360. The image processing section 320 performs various types of image processing such as white balance processing, demosaic (synchronization) processing, noise reduction, color conversion, tone conversion, contour enhancement and the like on the images output in sequence from the A/D conversion section 310, and outputs the processed images in sequence to the target object information acquisition section 340, the light amount determination section 370, and the display section 400. The system control section 330 inputs and outputs various control signals.

The target object information acquisition section 340 performs a detection process of a target object from the images output in sequence from the image processing section 320. The target object information acquisition section 340 outputs target object information generated based on the detection process to the focus drive mode setting section 350. The target object information acquisition section 340 will be described in detail later.

The focus drive mode setting section 350 sets the focus drive mode based on the target object information output from the target object information acquisition section 340, and outputs the information on the set focus drive mode to the focus control section 360. The focus drive mode setting section 350 also outputs the target object information to the focus control section 360. The focus drive mode setting section 350 will be described in detail later.

The focus control section 360 controls the focus lens 111 based on the information on the focus drive mode and the target object information which are output from the focus drive mode setting section 350. The focus control section 360 will be described in detail later.

The light amount determination section 370 determines the target amount of light from the light source, based on the images output in sequence from the image processing section 320, and outputs the determinations in sequence to a light source control section 510.

The display section 400 displays the images output in sequence from the image processing section 320. The display section 400 is, for example, a liquid crystal display or an electro-luminescence (EL) display.

The light source device 500 includes the light source control section 510 and the light source 520. The light source control section 510 controls the amount of light from the light source 520 in accordance with the target amounts of light from the light source output in sequence from the light amount determination section 370. The light source 520 emits illumination light. The light source 520 may be a xenon light source, a light emitting diode (LED), or a laser light source. The light source 520 may be another type of light source, without a limitation on light emission form.

1.2 Details of Processes

In a case of using the endoscopic system 20, a user who is a physician performs screening first. Upon discovery of a target object, the user approaches a scope to the object to perform detailed examination and diagnosis of the target object. The scope refers to the insertion section 100. The image in the present embodiment is an in-vivo image obtained by imaging the inside of a living body as described above, and the target object is specifically an in-vivo lesion. In this manner, it is possible to find a lesion and perform focus control suitable for detailed observation.

Hereinafter, an example in which the target object is a lesion will be described. However, the target object refers to an object that attracts more attention from the user than other objects and is not limited to a lesion. For example, if there is the need to closely examine a specific structure of a digestive canal or residues in the digestive canal, they may be set as target objects.

Figure 3:
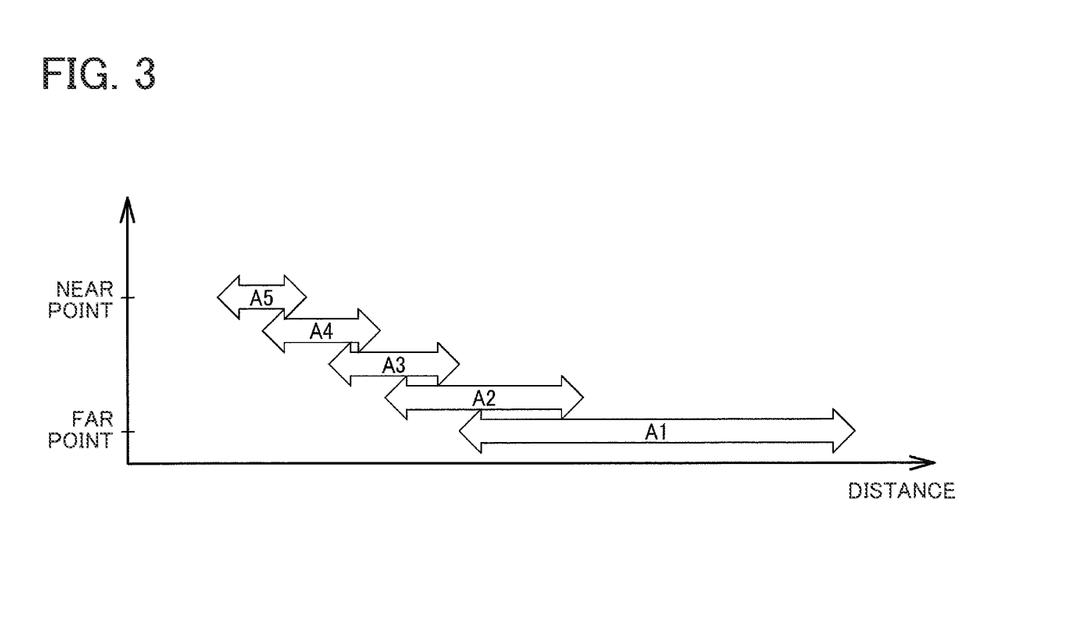
FIG. 3 illustrates depth-of-field ranges.

FIG. 3 is a diagram describing depth-of-field ranges in the present embodiment. In FIG. 3, the lateral axis indicates the distance from the objective optical system 110, where the left end corresponds to the position of the objective optical system 110, and the distance from the objective optical system 110 becomes longer in a rightward direction. The vertical axis indicates the in-focus object plane position. In the example of FIG. 3, on the vertical axis, the upper side corresponds to the near point side, and the lower side corresponds to the far point side. The near point refers to a point at which the in-focus object plane position is nearest to the objective optical system 110, and the far point is a point at which the in-focus object plane position is farthest from the objective optical system 110. Since the correspondence relationship between the position of the focus lens 111 and the in-focus object plane position is known in the design stage, the in-focus object plane position on the vertical axis in FIG. 3 can be replaced with the position of the focus lens 111.

In the endoscopic system 20, the optical system is designed such that, if the focus lens 111 is set to the farthest point, the depth of field not interfering with the screening of a lesion can be secured. In the example of FIG. 3, A1 denotes the depth of field at the far point. The range of the depth of field not interfering with screening can be determined in advance based on the expected usage situation of the endoscopic system 20. The characteristics of the objective optical system 110, the arrangement of the imaging element 120, and the like are determined such that the depth-of-field range A1 at the far point can cover the range of the depth of field not interfering with screening.

Upon discovery of a target object by screening, the user approaches the scope to the target object for detailed observation of the target object. However, since the depth of field is shallower with an increase in the number of pixels in the imaging element 120, it is not possible to sufficiently approach and observe the object with the in-focus object plane position fixed at the far point. Thus, the endoscopic system 20 performs focus adjustment. At this time, the endoscopic system 20 performs AF control to focus on the target object to present the image suitable for diagnosis and the like to the user. For example, the position of the focus lens 111 is adjusted by the AF control such that the appropriate depth-of-field range can be set among A2 to A5.

As above, the focus lens 111 is held at the far point (far end) at the time of screening, and an AF operation is executed for detailed observation of the lesion, whereby it is possible to provide the user with the image always focused on the object (lesion) attracting the user's attention while suppressing execution of useless AF operations. In the present embodiment, it is possible to realize appropriate focus control in accordance with the situations by setting the focus drive mode based on the detection results of the target object.

Figure 4:
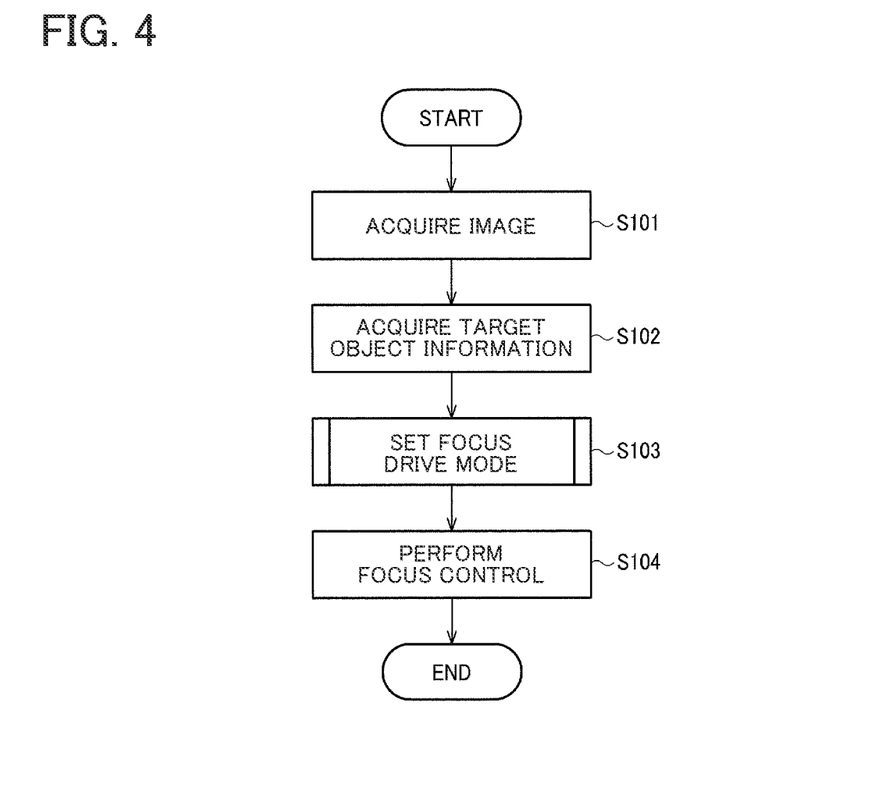
FIG. 4 is a flowchart of processing in the present embodiment.

Hereinafter, a specific process procedure will be described. FIG. 4 is a flowchart of a process in the present embodiment. When the process is started, first, in step S101, an image to be processed is acquired. Specifically, the processing in step S101 includes A/D conversion by the A/D conversion section 310 and various types of image processing by the image processing section 320.

Then, in step S102, the target object information acquisition section 340 acquires target object information on a lesion, based on the acquired image. Specifically, the target object information acquisition section 340 detects from the image the presence or absence of a lesion and the position of the lesion in the image. The target object information acquisition section 340 detects a lesion based on, for example, a feature amount of the image. The feature amount of the image here may relate to color, brightness, or a pattern on a surface structure. Alternatively, if information on a three-dimensional shape can be acquired, the target object information acquisition section 340 may detect a lesion based on a three-dimensional shape such as a concavo-convex shape.

The target object information acquisition section 340 may detect the presence or absence of a lesion and the position of the lesion in the image, based on a trained model. For example, a training device performs a training process on an image obtained by imaging the inside of a living body, using training data in which information for specifying the position of a lesion in the image is added as correct labels. The correct labels here are mask images in which the value of pixels corresponding to the position of the lesion is set to a first value and the value of other pixels are set to the second value different from the first value.

The training process is performed in accordance with a training algorithm to update parameters. The training algorithm here is an algorithm for determining output data through arithmetic operations on the input using existing parameters and executing a process of updating the parameters so as to decrease errors between the output data and the correct labels. For example, a backpropagation algorithm is widely known as a training algorithm using a neural network. The parameters in a neural network are weighting factors set between a node in a given layer (neuron) and a node in the next layer. In the case of using a convolutional neural network (CNN), the parameters may be filter characteristics that are used for convolutional operations.

The trained model includes parameters trained through an inference algorithm and the above-described training process. The inference algorithm is an algorithm for executing an inference process of determining output data based on inputs and parameters. For example, the endoscopic system 20 includes an unillustrated storage section that stores trained models. The target object information acquisition section 340 performs a process of detecting a lesion from an image by reading a trained model from the storage section and operating in accordance with the trained model. Some or all of the trained models may be stored in an external device such as a server system.

The target object information acquisition section 340 outputs lesion detection information and lesion position information as target object information. The lesion detection information is information indicating the presence or absence of a lesion. The lesion position information is information specifying the position of the lesion on the image. The lesion position information may be information on coordinate values representing the lesion or information corresponding to a mask image.

Figure 5:
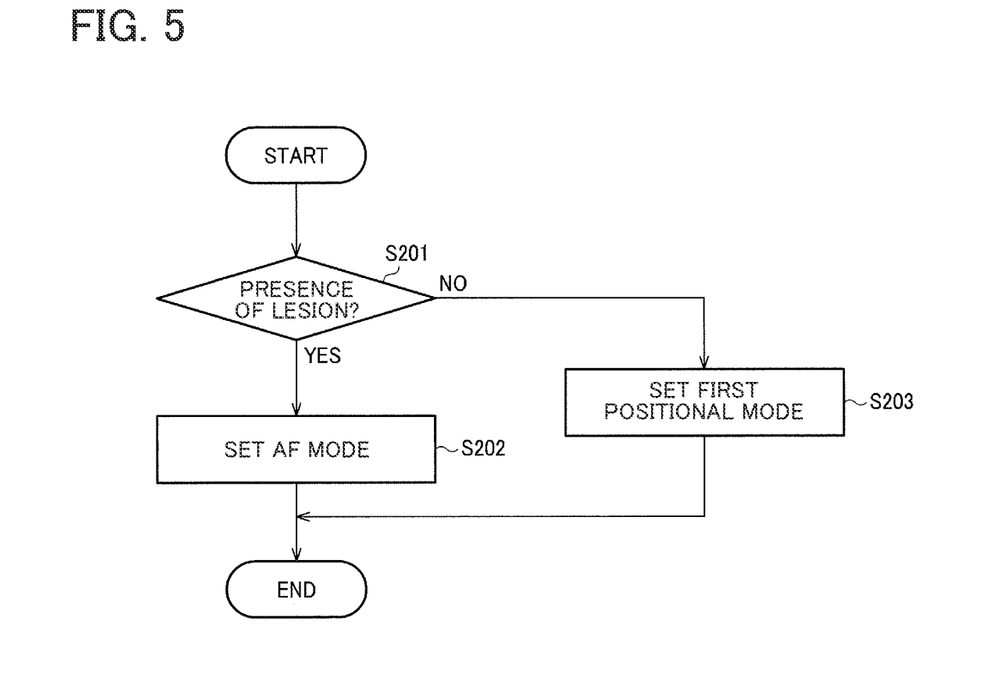
FIG. 5 is a flowchart of a setting process of a focus drive mode.

Next, in step S103, the focus drive mode setting section 350 sets the focus drive mode based on the target object information. FIG. 5 is a flowchart of the focus drive mode setting process in step S103. First, in step S201, the focus drive mode setting section 350 determines the presence or absence of a lesion, based on the lesion detection information acquired from the target object information acquisition section 340. If a lesion is detected, in step S202, the focus drive mode setting section 350 sets the focus drive mode to the AF mode. If no lesion is detected, in step S203, the focus drive mode setting section 350 sets the focus drive mode to a first positional mode.

The first positional mode in the present embodiment is a focus drive mode in which an in-focus object plane position is set at a position remote from (on the far point side of) a given reference position in a set range of the in-focus object plane position in the objective optical system 110 including the focus lens 111. The reference position here is a position within the set range of the in-focus object plane position, and specifically, is a given position remote from (on the far point side of) a central position. That is, the first positional mode is a mode in which the in-focus object plane position is set at a relatively remote position in the case of using the objective optical system 110 that can adjust the in-focus object plane position within a given range. The position remote from a given reference position is, in a narrow sense, a far point that is most remote from the objective optical system 110 in the set range of the in-focus object plane position. This makes it possible to focus on even an object remote from the scope, thereby capturing an image suitable for screening. In addition, since setting the in-focus object plane position at a remote position increases the depth of field, even an object close to the objective optical system 110 can be focused on to an extent that screening is possible.

Returning to FIG. 4 to continue the description, after setting the focus drive mode, in step S104, the focus control section 360 performs a focus control in accordance with the focus drive mode. If the focus drive mode is the AF mode, the focus control section 360 sets the AF area based on the lesion position information. Specifically, the focus control section 360 sets a given image area including the lesion, as the AF area. The focus control section 360 then executes the AF operation based on the information on the AF area in the image output from the A/D conversion section 310. The AF method is, for example, a contrast method, and the focus control section 360 moves the focus lens 111 to the lens position where the contrast value calculated from the AF area is maximum. The AF method may be a phase-difference method, and publicly known AF techniques can be widely applicable. The AF here specifically refers to a video AF by which the focus lens 111 is continuously moved based on consecutive frame images.

If the focus drive mode is the first positional mode, the focus control section 360 moves the focus lens 111 to a given position and holds there. As described above, the lens position here is the position where the in-focus object plane position is most distant in the settable range, and specifically, the lens position is the far end.

Accordingly, at the time of screening, using the first positional mode makes it possible to present an in-focus image of a range that is suitable for screening. At the time of detailed observation, using the AF mode makes it possible to present an image focused on the target object. Since the focus drive mode is set on the basis of the detection results of the target object, it is possible to always provide an in-focus image of the area the user wishes to observe without the need for user operations. In addition, since the detection of the target object is a condition for shifting to the AF mode, it is possible to suppress useless AF operations.

The method in the present embodiment reduces a burden on the user in focus adjustment but is not intended to inhibit user operations. For example, after the focus lens 111 is moved to the far end by the focus control in accordance with the first positional mode, the user may perform an explicit operation to move the focus lens 111. That is, the focus adjustment may be performed in a manual focus (MF) mode. In addition, during the focus control in the AF mode, it is not inhibited that the focus drive mode is shifted to the MF mode with a user operation or the like as a trigger.

The method in the present embodiment is applicable to the endoscopic system 20 illustrated in FIG. 2. The endoscopic system 20 includes the focus control device 10 (the processing section 300) and the objective optical system 110 including the focus lens 111. According to the method in the present embodiment, it is possible to perform the focus control suitable for observation using the endoscopic system 20.

The process performed by the focus control device 10 in the present embodiment may be implemented as a focus control method. The focus control method includes: a step of acquiring an image of an inside of a living body; a step of acquiring target object information on a target object from the image; a step of setting a focus drive mode based on the target object information; and a step of performing a focus control based on the focus drive mode. According to the focus control method, if the target object is detected in the image, the focus drive mode is set to the AF mode in which the focus lens is controlled to focus on the target object. In addition, according to the focus control method, if the target object is not detected in the image, the focus drive mode is set to a first positional mode in which the focus lens 111 is held at a predetermined lens position.

2. Second Embodiment

Next, a second embodiment will be described. A configuration of a focus control device 10 is similar to that illustrated in FIG. 1. A method in the second embodiment is also applicable to an endoscopic system 20. An entire configuration of the endoscopic system 20 is similar to that illustrated in FIG. 2.

First, the present embodiment will be described. After discovery of a lesion, while the lesion is closely examined and diagnosed, the lesion may temporarily become invisible in the image because the lesion falls out of the imaging range or becomes hidden behind folds in the alimentary canal. When the lesion temporarily disappears from the image, if a focus lens 111 is moved to the far end, the image may be severely blurred to interfere with the observation. The severe blurring refers to the state of the image in which the degree of focus is significantly lowered.

In the second embodiment, if the lesion becomes no longer detected, it is determined whether the disappearance is temporary. The non-temporary disappearance means, for example, that the user has ended the detailed observation of the lesion and shifted to screening. If it is determined that the lesion has temporarily disappeared from view, the focus control device 10 (a processing section 300) controls the focus lens 111 such that the image does not become severely blurred. This allows the user to continue the observation without a feeling of strangeness and start the AF operation immediately after the lesion appears again in the image.

Figure 6:
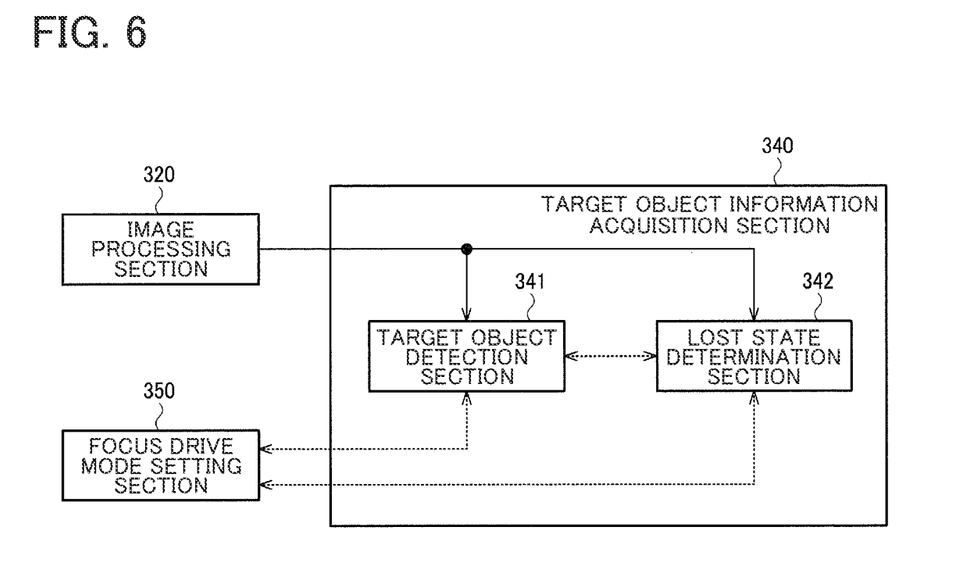
FIG. 6 illustrates a configuration example of a target object information acquisition section.

FIG. 6 is a diagram illustrating a configuration example of a target object information acquisition section 340 in the present embodiment. The target object information acquisition section 340 includes a target object detection section 341 and a lost state determination section 342.

The target object detection section 341 detects from the image the presence or absence of a lesion and the position of the lesion in the image. That is, the target object detection section 341 performs a process similar to that performed by the target object information acquisition section 340 in the first embodiment. The target object detection section 341 may detect the lesion using the feature amount of the image or may detect the lesion using a trained model.

The lost state determination section 342 analyzes the detection results of the target object in time sequence to determine whether the target object is in a lost state where the target object is temporarily invisible in the image. The time-sequence analysis refers to a process based on information at two timings at least. The information at two timings may be time-difference information between the two timings or may be information based on the images acquired at the two timings. The two timings here are, in a narrow sense, one timing at which the target object was lastly detected and the other timing when the target object became no longer detected. The detection results of the target object are lesion detection information output from the target object detection section 341. In this manner, it is possible to determine whether the undetected state of the lesion in the image is temporary. Hereinafter, information indicating the result of the determination on the lost state will be called lost-state determination information.

For example, the lost state determination section 342 determines that the target object is in the lost state until after a lapse of a given period of time since the detected target object became no longer detected. The temporary disappearance of the lesion occurs, for example, if the positional relationship between the scope and the object becomes disturbed due to a user's operation error or the like, or if a treatment tool shifts from the position where it has lifted folds. In these cases, since it is assumed that the user will immediately adjust the position of the scope or reposition the treatment tool to lift the folds, the lesion will be detected again in a short time. That is, standby for a certain time makes it possible to suppress erroneous determination of the temporarily undetected state of the lesion as shift to the screening.

Alternatively, for example, the lost state determination section 342 may determine that the target object is in the lost state if the detected target object becomes no longer detected and the change in the image from the state where the target object was detected is equal to or less than a given threshold. For example, the lost state determination section 342 further includes a motion calculation section that calculates global motion from the image. If a state change occurs from the state with the lesion detected to the state with the lesion undetected, the motion calculation section calculates global motion between the two states. If the global motion is equal to or less than the predetermined threshold, the lost state determination section 342 determines that the target object is in the lost state. In this case, the lost state determination section 342 may determine that the target object is not in the lost state once the global motion becomes equal to or greater than the predetermined threshold. Specifically, the global motion refers to broad motion relative to motion that is determined from a small area in the image. For example, in the case of determining motion information based on block matching, the information on global motion is motion information that is determined using blocks of a size with a predetermined or larger proportion of the entire image. In a narrow sense, the information on global motion is information that is determined through block matching in the entire image.

At the end of detailed observation, for example, the user may resume screening so that the positional relationship between the scope and the object greatly changes. In contrast, if the target object temporarily falls outside the imaging range due to the user's operation error, the amount of movement of the scope relative to the object is comparatively small. If the object is hidden behind folds returned from the lifted position, the motion seen in the image is limited to the areas of the folds and the treatment tool, and the broad motion is small. That is, if the lesion temporarily disappears from view, the global motion is considered to be smaller than at the end of the observation. Thus, it is possible to appropriately determine the lost state by the global motion as described above.

In the lost state, the positional relationship between the scope and the object does not change to an extreme. Therefore, as stated above, if the focus lens 111 is moved to the far end, the image may become severely blurred to interfere with the observation. Accordingly, if the target object information acquisition section 340 determines that the target object is in the lost state, a focus drive mode setting section 350 sets the focus drive mode to a mode other than the first positional mode. The focus control device 10 and the endoscopic system 20 in the present embodiment have a plurality of focus drive modes including the first positional mode. In the lost state, out of the plurality of focus drive modes, a mode other than the first positional mode is used. This suppresses at least the severe blurring of the image so that the user can continue observation in a stable manner.

Figure 7:
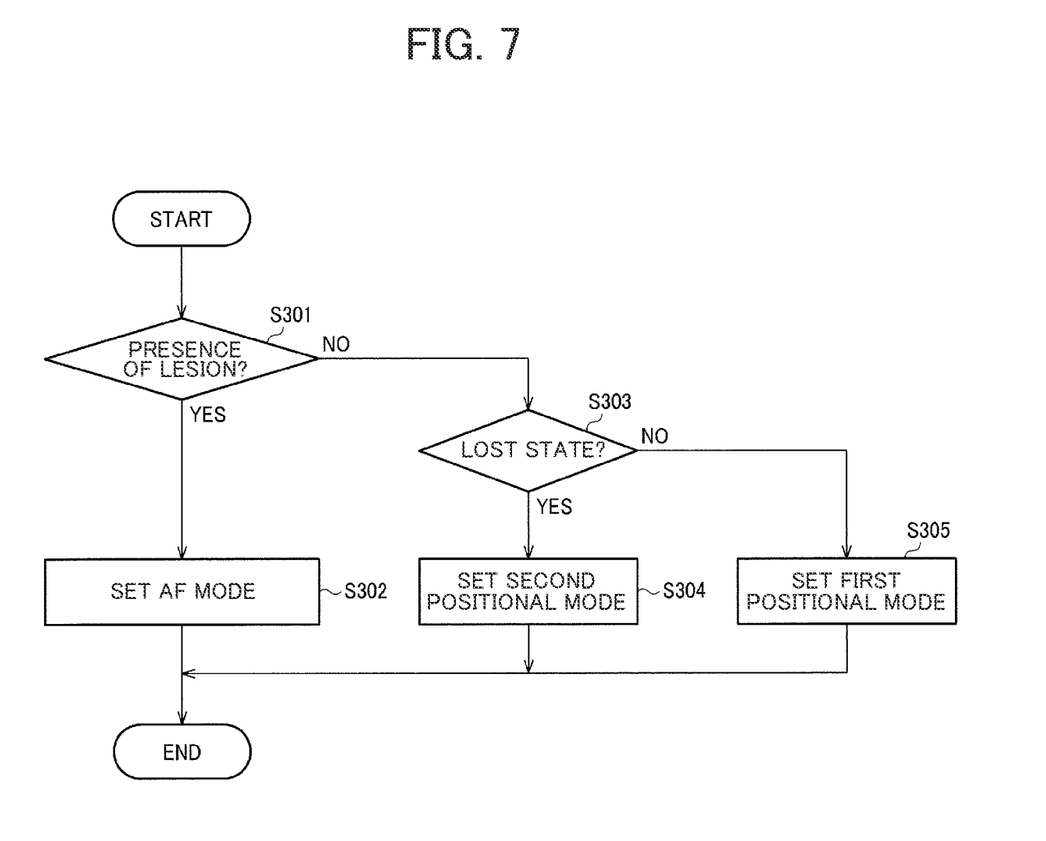
FIG. 7 is a flowchart of a setting process of the focus drive mode taking a lost state into consideration.

FIG. 7 is a flowchart of a setting process of the focus drive mode in the second embodiment. First, in step S301, the focus drive mode setting section 350 determines the presence or absence of a lesion based on the lesion detection information acquired from the target object information acquisition section 340. If the lesion is detected, in step S302, the focus drive mode setting section 350 sets the focus drive mode to the AF mode. Steps S301 and S302 are similar to steps S201 and S202 illustrated in FIG. 5.

If the lesion is not detected, in step S303, the focus drive mode setting section 350 determines whether the target object is in the lost state based on the lost state determination information acquired from the target object information acquisition section 340. If determining that the target object is not in the lost state, in step S305, the focus drive mode setting section 350 sets the focus drive mode to the first positional mode. Step S305 is similar to step S203 illustrated in FIG. 5.

If determining in step S303 that the target object is in the lost state, in step S304, the focus drive mode setting section 350 sets the focus drive mode to a second positional mode. The second positional mode is a mode in which the focus lens 111 is held at a position different from the lens position in the first positional mode. The lens position in the second positional mode is, for example, a lens position at which it was determined in step S301 that there was no lesion. While the lesion is detected, it is considered that the state of focusing on the lesion will be maintained by the focus control in the AF mode. Even in the lost state, maintaining the lens position at that time can suppress severe blurring of the image.

However, the lens position in the second positional mode is not limited to this. For example, the lens position in the second positional mode may be a fixed lens position at which the in-focus object plane position is nearer to the objective optical system 110 than the far point. In the example of FIG. 3, the lens position in the second positional mode is a position of the focus lens 111 that achieves any of the depth-of-field ranges A2 to A5. In this case, in the second positional mode, the object on the near point side is more likely to be in focus than in the first positional mode. Therefore, it is possible to suppress severe blurring of the image in the lost state where the detailed observation of the target object will be highly probably continued.

Figure 8:
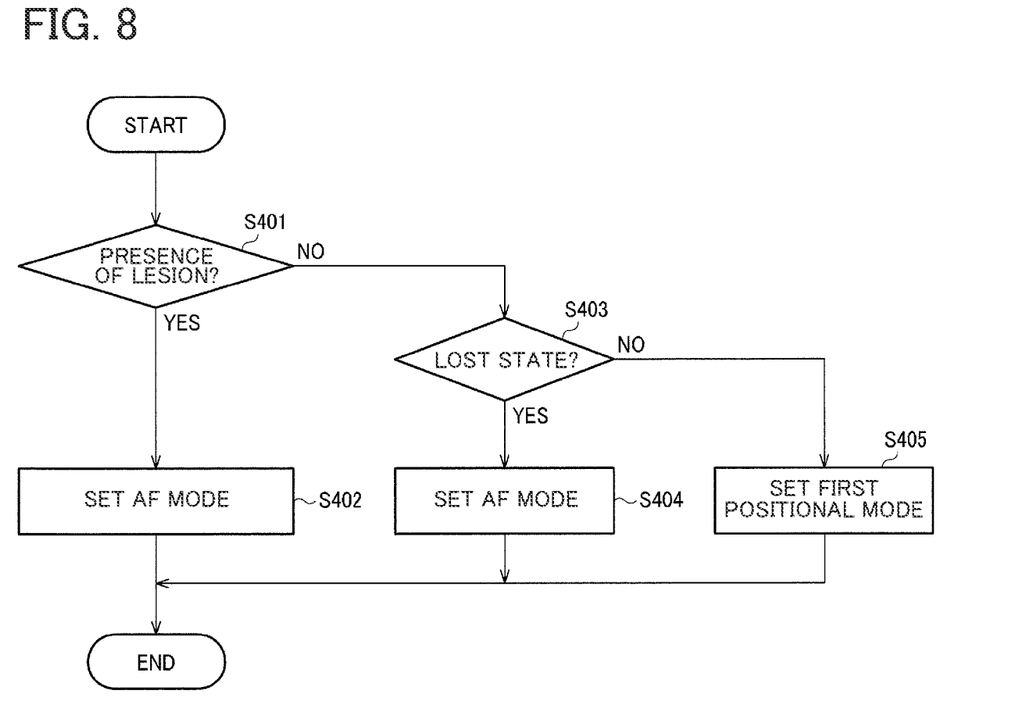
FIG. 8 is a flowchart of a setting process of the focus drive mode taking the lost state into consideration.

FIG. 8 is a flowchart of a modification example of the setting process of the focus drive mode in the second embodiment. Steps S401 to S403 and S405 are similar to steps S301 to S303 and S305 illustrated in FIG. 7.

If determining in step S403 that the target object is in the lost state, in step S404, the focus drive mode setting section 350 may set the focus drive mode to the AF mode. Maintaining the AF mode even in the lost state keeps the state of the AF area being focused on, thereby suppressing severe blurring of the image. However, since the lesion is not detected in the lost state, the AF area cannot be set based on the lesion position information. Accordingly, a focus control section 360 sets a predetermined area in the image as the AF area. The predetermined area is, for example, a central area in the image. Alternatively, the focus control section 360 may set the AF area based on an image output from an A/D conversion section 310. For example, the focus control section 360 determines a right exposure area from the brightness information of the image, and sets the area as the AF area.

3. Third Embodiment

Next, a third embodiment will be described. A configuration of a focus control device 10 is similar to that illustrated in FIG. 1. A method in the third embodiment is also applicable to an endoscopic system 20. An entire configuration of the endoscopic system 20 is similar to that illustrated in FIG. 2.

First, the present embodiment will be described. After discovery of a lesion, while the lesion is closely examined and diagnosed, the lesion is in focus if the lesion is located within a depth-of-field range in a first positional mode. In this case, maintaining the first positional mode without shifting to an AF mode suppresses execution of useless AF operations.

Figure 9:
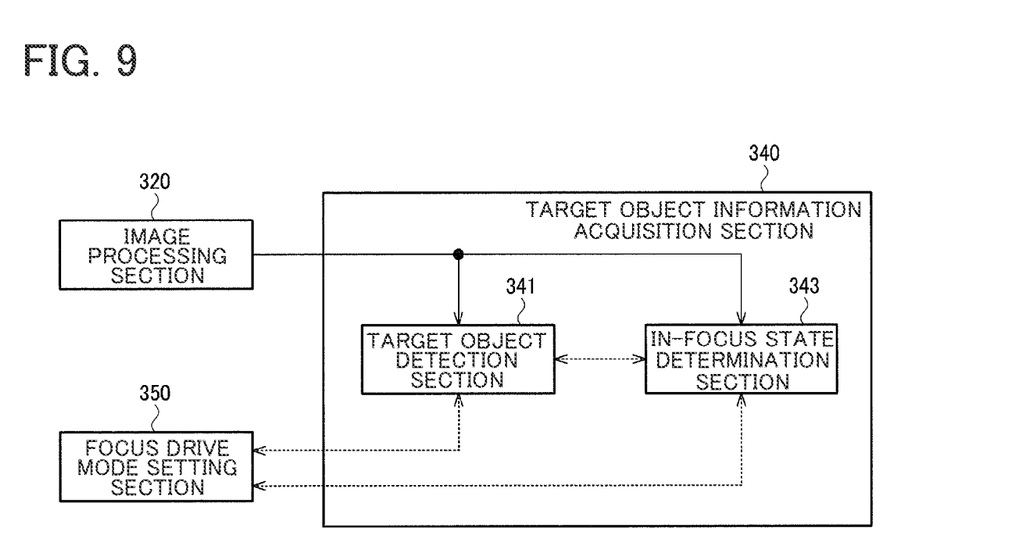
FIG. 9 illustrates another configuration example of the target object information acquisition section.

FIG. 9 is a diagram illustrating a configuration example of a target object information acquisition section 340 in the present embodiment. The target object information acquisition section 340 includes a target object detection section 341 and an in-focus state determination section 343. As in the second embodiment, the target object detection section 341 outputs lesion detection information and lesion position information.

The in-focus state determination section 343 determines whether the lesion is within a depth-of-field range, based on the lesion detection information output from the target object detection section 341, and outputs in-focus state information as a determination result. The depth-of-field range here is the depth-of-field range in the first positional mode as stated above.

The in-focus state determination section 343 determines whether the target object is within the depth-of-field range, for example, based on the size of the target object in the image. For example, if the target object is a given lesion, it is possible to predict from the medical viewpoint the range within which the actual size of the lesion will fall. Even if the target object is not a lesion, the typical size of the target object may be predictable in some cases. In such cases, based on the size of the target object in the image, the distance between the target object and an objective optical system 110 (an imaging element 120) can be estimated. Since the depth-of-field range in the first positional mode is known from the design, it is possible to determine whether the target object is within the depth-of-field range by comparing the depth-of-field range with the estimated distance.

Alternatively, the in-focus state determination section 343 may determine whether the target object is within the depth-of-field range, for example, based on the degree of blurring of the target object in the image. For example, the in-focus state determination section 343 calculates an evaluation value of the degree of blurring such as a contrast value, based on the area including the lesion in the image. If the contrast value is equal to or greater than a predetermined threshold, the in-focus state determination section 343 determines that the target object is within the depth-of-field range.

Otherwise, the in-focus state determination section 343 may determine whether the target object is within the depth-of-field range, for example, based on information on the distance to the target object. The distance information is determined, for example, by using a distance meter not illustrated. The distance measurement may be performed by using, for example, a Time-of-Flight (ToF) method or stereo matching. Instead, any other distance measurement method may be used. As stated above, since the depth-of-field range in the first positional mode is known from the design, it is possible to determine whether the target object is within the depth-of-field range based on the distance information.

Figure 10:
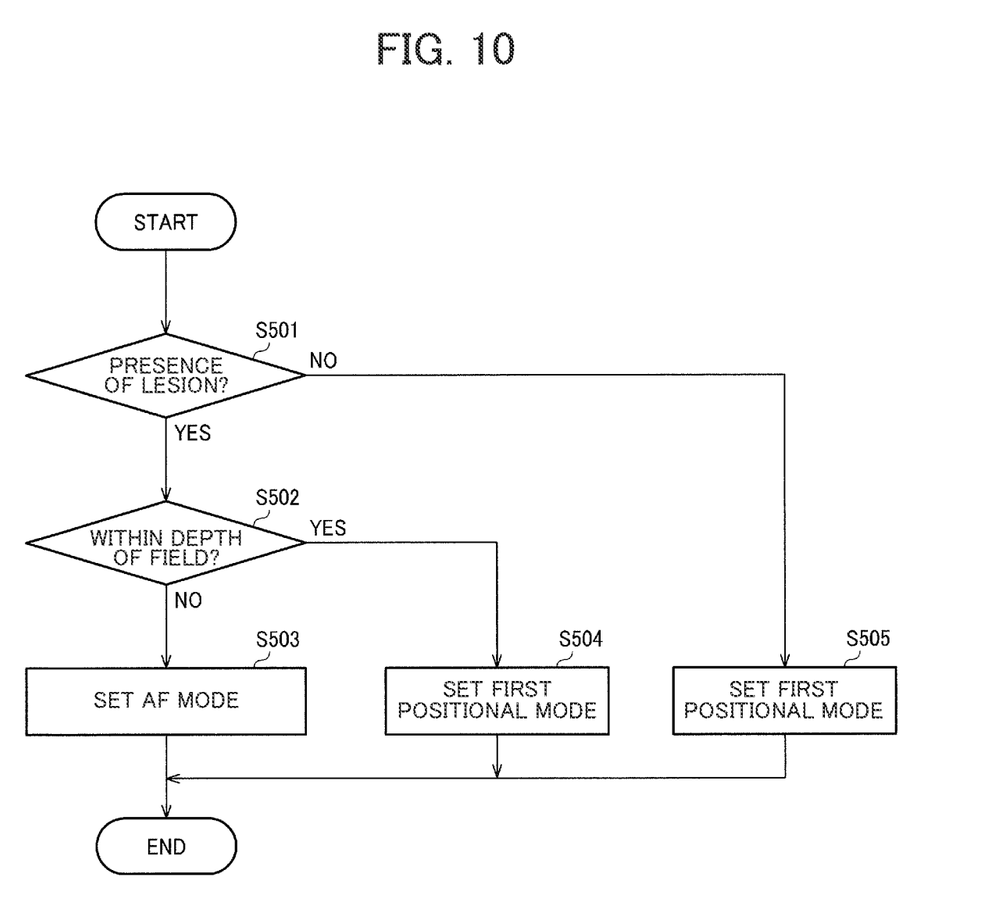
FIG. 10 is a flowchart of a setting process of a focus drive mode taking an in-focus state of a target object into consideration.

FIG. 10 is a flowchart of a setting process of the focus drive mode in the third embodiment. First, in step S501, a focus drive mode setting section 350 determines the presence or absence of a lesion based on lesion detection information acquired from the target object information acquisition section 340. If the lesion is not detected, in step S505, the focus drive mode setting section 350 sets the focus drive mode to the first positional mode. Steps S501 and S505 are similar to steps S201 and S203 illustrated in FIG. 5.

If the lesion is detected, in step S502, the focus drive mode setting section 350 determines whether the detected target object is within the depth-of-field range, based on the in-focus state determination information acquired from the target object information acquisition section 340. If the target object is within the depth-of-field range, in step S504, the focus drive mode setting section 350 sets the focus drive mode to the first positional mode. That is, even though the target object information acquisition section 340 detects the target object, if determining that the target object is within the depth-of-field range, the focus drive mode setting section 350 sets the focus drive mode to the first positional mode. On the other hand, if determining that the target object is not within the depth-of-field range, in step S503, the focus drive mode setting section 350 sets the focus drive mode to the AF mode. That is, if maintaining the first positional mode causes blurring of the target object in the image, the focus control in the AF mode is started.

According to the method in the present embodiment, unnecessary AF operations can be suppressed. Therefore, it is possible to stabilize the operations of the focus control device 10 and suppress wearing of the actuator 130.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. A focus control device comprising:
one or more processors configured to:
acquire images from an endoscope, the endoscope including a focus lens configured to change an in-focus object plane position of an in-vivo image, and an imaging element configured to capture light and output signal based on the captured light, wherein the images from the endoscope are generated based on the signal;
detect target object information from the images;
analyze detection results of a target object in time sequence to determine whether the target object is in a lost state in which the target object is not temporarily captured in the images;
control the focus lens of the endoscope to automatically focus on the target object in a case where the target object is detected;
arrange the focus lens at a first fixed position that is within a set range of an in-focus object plane position and is on the far point side of a central position in a case where the target object is not detected and is not in the lost state; and
set the focus lens of the endoscope at a second fixed position that is nearer to a near point than the first fixed position or control the focus lens of the endoscope so as to automatically focus on the target object in a case where the lost state is determined.

2. The focus control device as defined in claim 1, wherein the second fixed position is a lens position at which the target object detected by the one or more processors has become no longer detected.

3. The focus control device as defined in claim 1, wherein the one or more processors are configured to determine that the target object is in the lost state until after a lapse of a predetermined period of time since the detected target object has become no longer detected.

4. The focus control device as defined in claim 1, wherein the one or more processors are configured to determine that the target object is in the lost state in a case where the detected target object becomes no longer detected and a change in the images since detection of the target object is equal to or less than a predetermined threshold.

5. The focus control device as defined in claim 1, wherein the one or more processors are configured to:
determine whether the target object is located within a depth-of-field range; and
even when the the target object is detected, in a case where it is determined that the target object is within the depth-of-field range, arrange the focus lens at the first fixed position.

6. The focus control device as defined in claim 5, wherein the one or more processors are configured to determine whether the target object is within the depth-of-field range based on a size of the target object in the images.

7. The focus control device as defined in claim 5, wherein the one or more processors are configured to determine whether the target object is within the depth-of-field range based on a degree of blurring of the target object in the images.

8. The focus control device as defined in claim 5, wherein the one or more processors are configured to determine whether the target object is within the depth-of-field range based on information on a distance to the target object.

9. The focus control device as defined in claim 1, wherein the target object is a lesion in a living body.

10. A method performed by one or more processors of a focus control device, the method comprising:
acquiring images from an endoscope, the endoscope including a focus lens configured to change an in-focus object plane position of an in-vivo image, and an imaging element configured to capture light and output signals based on the captured light, wherein the images from the endoscope are generated based on the signal;
detecting target object information from the images;
analyzing detection results of the target object in time sequence to determine whether the target object is in a lost state in which the target object is not temporarily captured in the images;
controlling the focus lens of the endoscope to automatically focus on the target object in a case where the target object is detected;
arranging the focus lens at a first fixed position that is within a set range of an in-focus object plane position and is on the far point side of a central position in a case where the target object is not detected and is not in the lost state; and
setting the focus lens of the endoscope at a second fixed position that is nearer to a near point than the first fixed position or controlling the focus lens of the endoscope so as to automatically focus on the target object in a case where the lost state is determined.

11. A non-transitory computer-readable storage medium that stores an operation program that causes one or more processors of a focus control device to at least perform:
acquiring images from an endoscope, the endoscope including a focus lens configured to change an in-focus object plane position of an in-vivo image, and an imaging element configured to capture light and output signals based on the captured light, wherein the images from the endoscope are generated based on the signal;
detecting target object information from the images;
analyzing detection results of the target object in time sequence to determine whether the target object is in a lost state in which the target object is not temporarily captured in the images;

controlling the focus lens of the endoscope to automatically focus on the target object in a case where the target object is detected;

arranging the focus lens at a first fixed position that is within a set range of an in-focus object plane position and is on the far point side of a central position in a case where the target object is not detected and is not in the lost state; and setting the focus lens of the endoscope at a second fixed position that is nearer to a near point than the first fixed position or controlling the focus lens of the endoscope so as to automatically focus on the target object in a case where the lost state is determined.

* * * * *